US011350920B1

(12) United States Patent
Dewey

(10) Patent No.: US 11,350,920 B1
(45) Date of Patent: Jun. 7, 2022

(54) MODULAR RETRACTOR, SYSTEM, AND METHOD

(71) Applicant: Warsaw Orthopedic, Inc., Warsaw, IN (US)

(72) Inventor: Jonathan M. Dewey, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/104,897

(22) Filed: Nov. 25, 2020

(51) Int. Cl.
*A61B 17/02* (2006.01)

(52) U.S. Cl.
CPC ...... *A61B 17/0206* (2013.01); *A61B 17/0218* (2013.01)

(58) Field of Classification Search
CPC .. A61B 17/02; A61B 17/0206; A61B 17/0218
See application file for complete search history.

(56) References Cited

U.S. PATENT DOCUMENTS

| | | | | |
|---|---|---|---|---|
| 4,130,113 A * | 12/1978 | Graham | ............. | A61B 17/0293 600/224 |
| 5,377,667 A * | 1/1995 | Patton | ............. | A61B 1/32 600/184 |
| 6,945,933 B2 * | 9/2005 | Branch | ............. | A61B 17/0206 600/210 |
| 7,976,463 B2 * | 7/2011 | Dewey | ............. | A61B 17/0206 600/210 |
| 9,084,591 B2 * | 7/2015 | Reglos | ............. | A61B 17/0293 |
| 2007/0156024 A1 * | 7/2007 | Frasier | ............. | A61B 17/02 600/219 |
| 2008/0249372 A1 * | 10/2008 | Reglos | ............. | A61B 17/0293 600/205 |
| 2010/0081885 A1 * | 4/2010 | Wing | ............. | A61B 17/7076 600/215 |
| 2011/0237903 A1 * | 9/2011 | Fehling | ............. | A61B 17/0293 600/233 |
| 2013/0090533 A1 * | 4/2013 | Jaeger | ............. | A61B 1/32 600/224 |
| 2014/0275801 A1 * | 9/2014 | Menchaca | ............. | A61B 17/0218 600/212 |
| 2015/0045626 A1 * | 2/2015 | Reimels | ............. | A61B 17/0206 600/213 |
| 2017/0340866 A1 * | 11/2017 | Richard | ............. | A61B 17/3439 |

* cited by examiner

*Primary Examiner* — Julianna N Harvey
*Assistant Examiner* — Holly Joanna Lane
(74) *Attorney, Agent, or Firm* — Fox Rothschild LLP; P. Marshall Ticer

(57) ABSTRACT

A modular retractor system may include a first annular retainer and a second annular retainer defining a central axis projecting through a first center point of the first annular retainer and a second center point of the second annular retainer. The modular retractor may further include a plurality of primary blades, pivotally coupled to the first annular retainer and an adjacent primary blade of the plurality of primary blades. In some embodiments, the first annular retainer may be configured to, selectively, radially contract towards the first center point such that each of the plurality of primary blades articulates with respect to the central axis. In some embodiments, the second annular retainer may circumscribe the outside of the plurality of primary blades and be configured to apply a biasing force against each of the plurality of primary blades towards the central axis. Additionally, a plurality of supplemental blades may be provided.

19 Claims, 15 Drawing Sheets

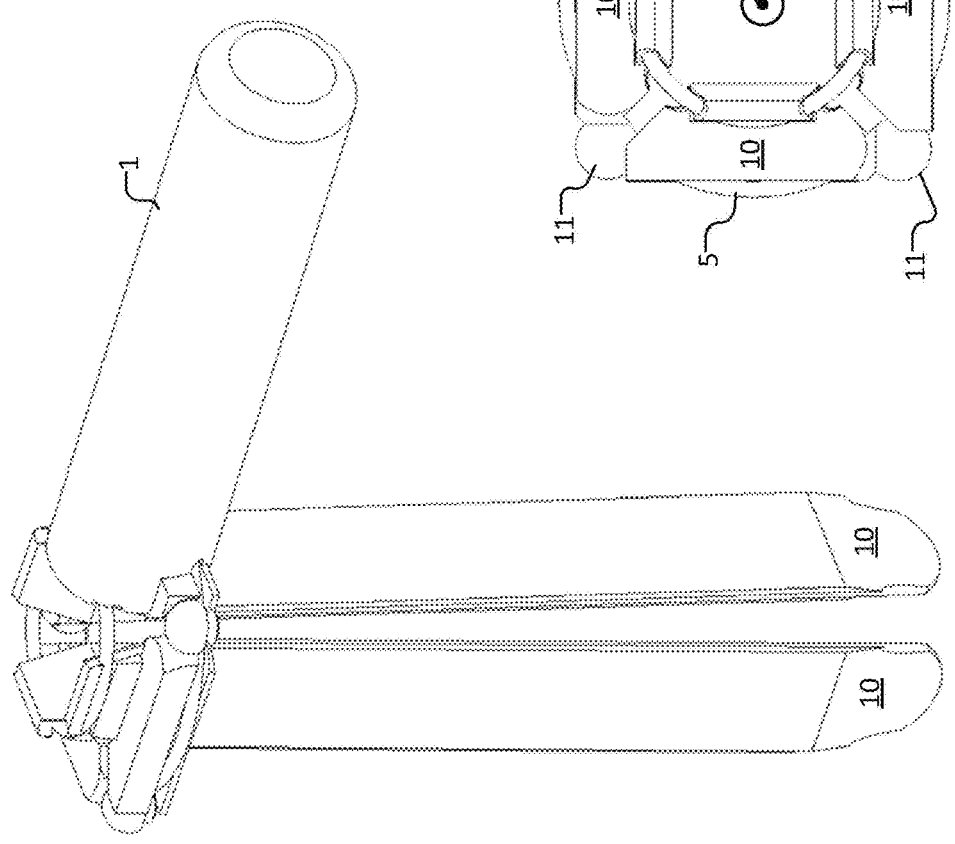
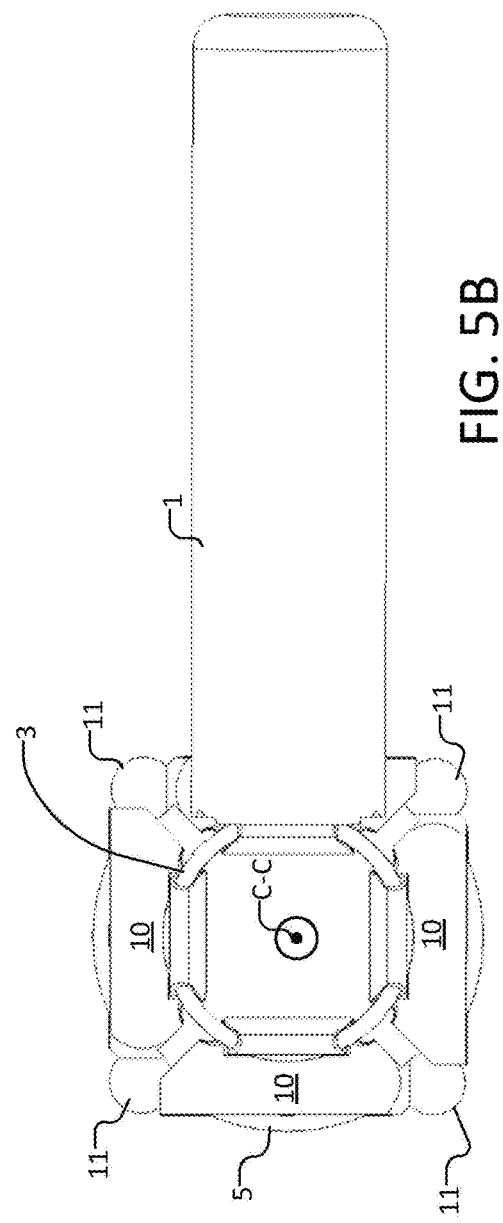
FIG. 5A
FIG. 5B

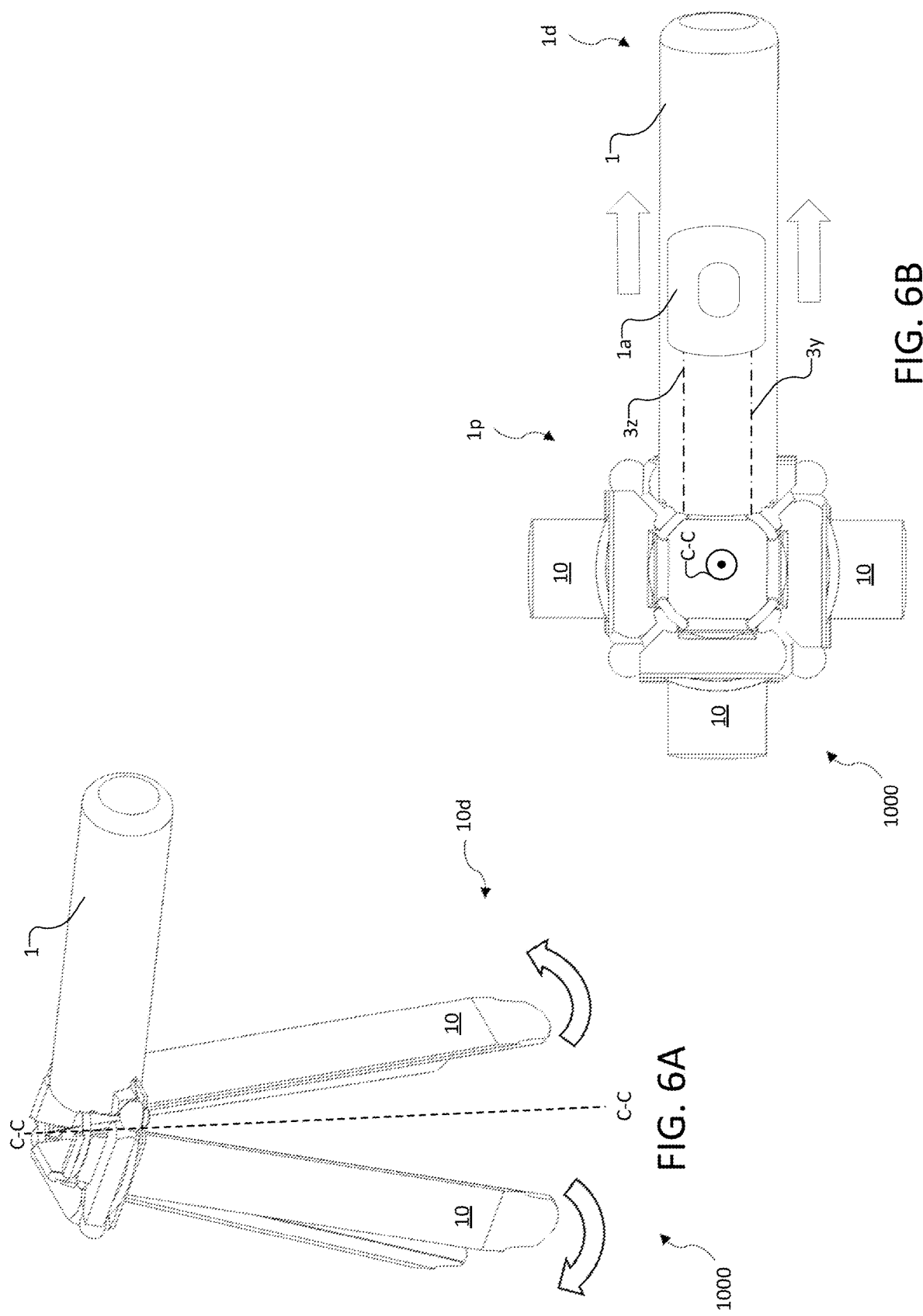

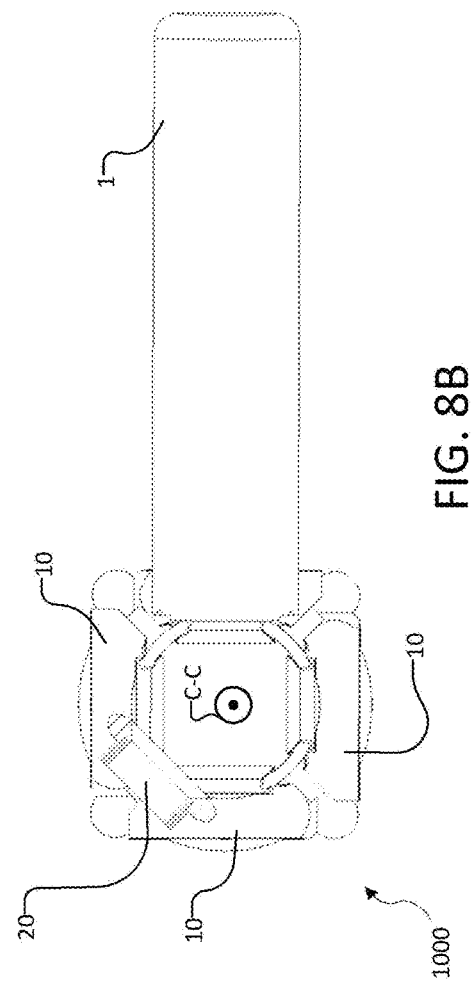
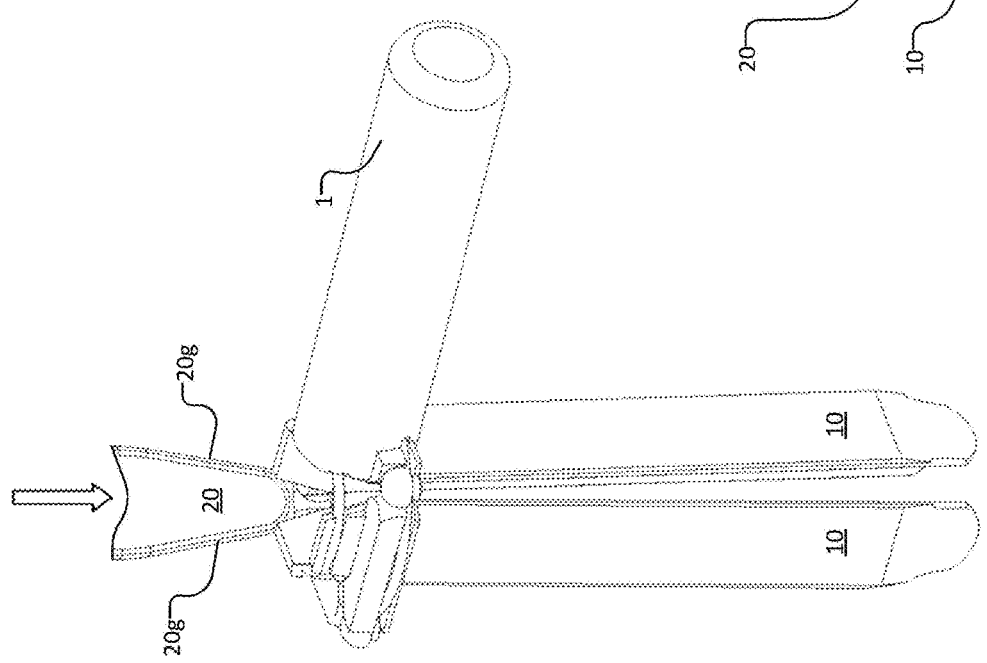

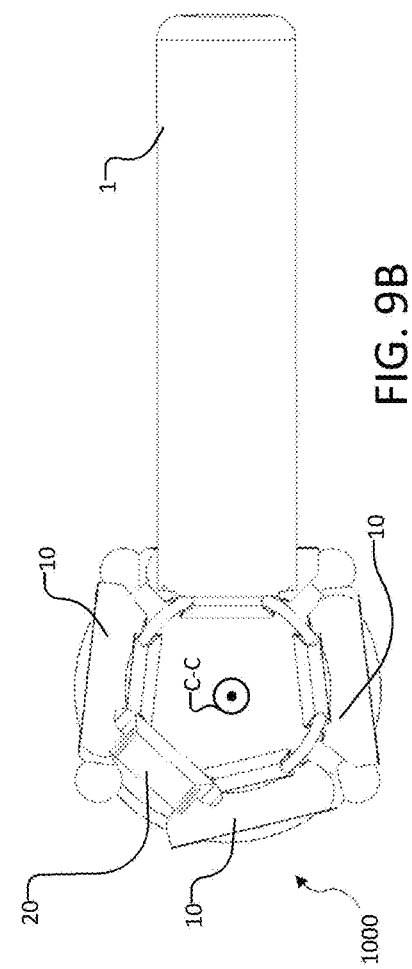
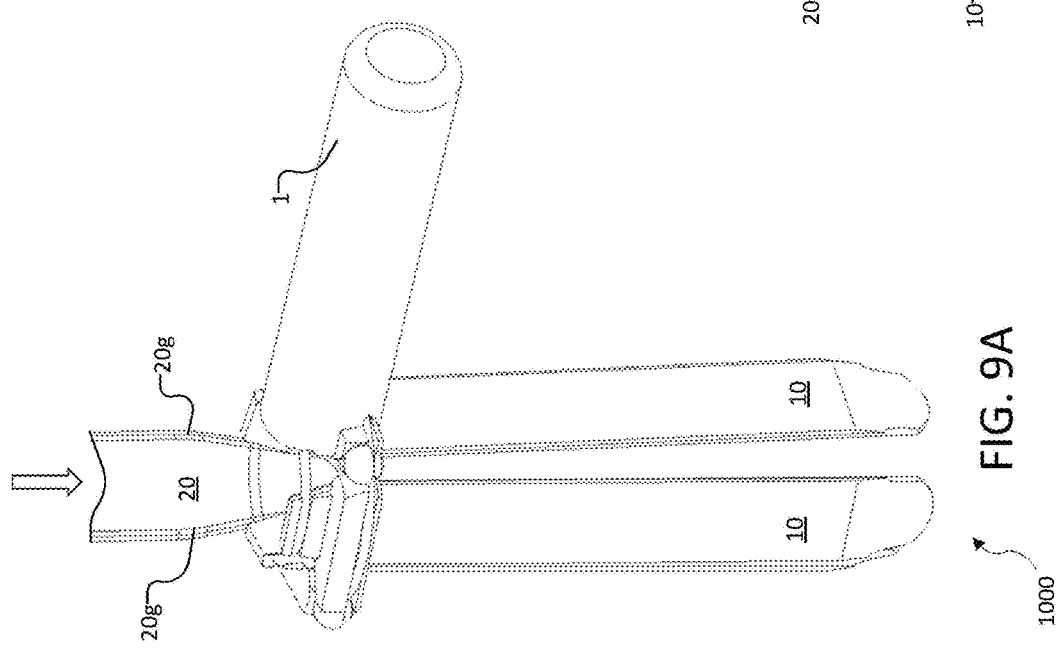

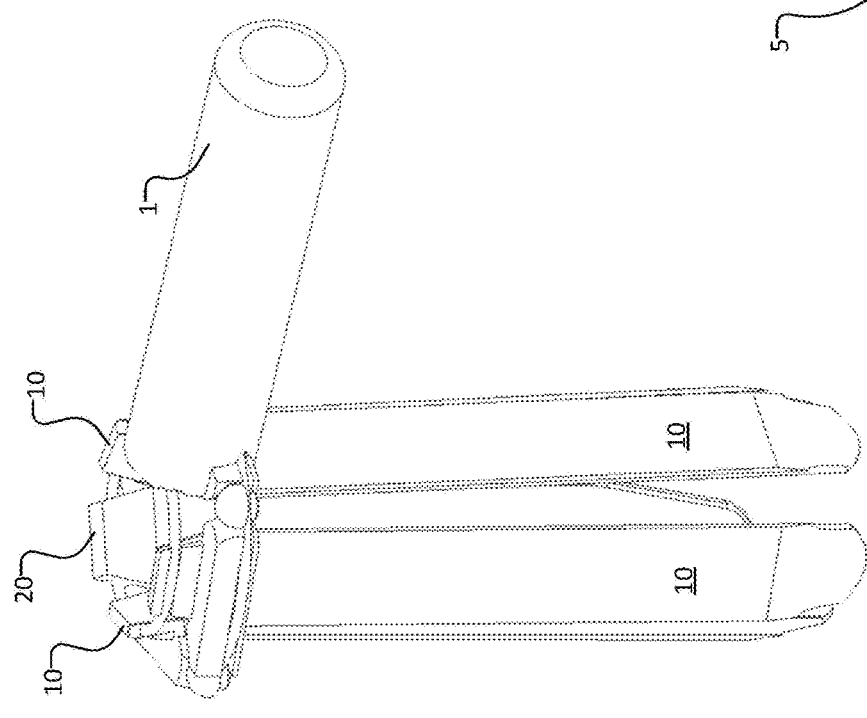
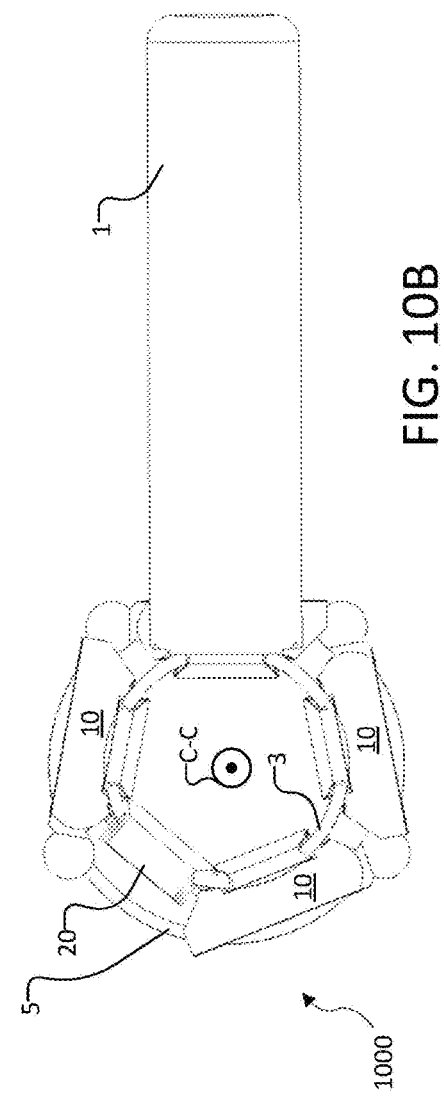
FIG. 10A
FIG. 10B

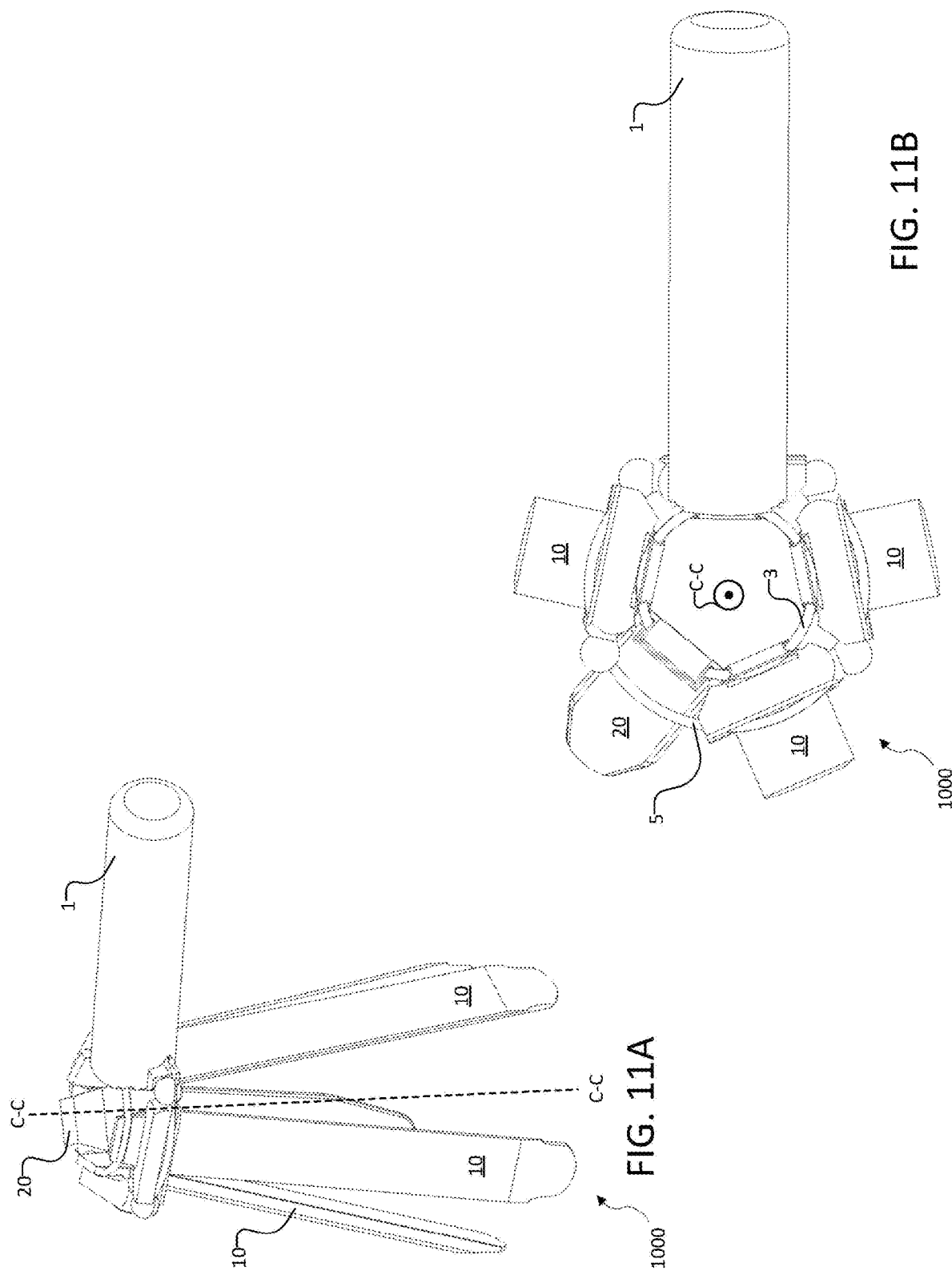

MODULAR RETRACTOR, SYSTEM, AND METHOD

CROSS REFERENCE TO RELATED APPLICATIONS

This Application hereby incorporates the disclosure of each of U.S. Pat. No. 7,976,463, titled INSTRUMENTS AND METHODS FOR MINIMALLY INVASIVE TISSUE RETRACTION AND SURGERY, filed Jan. 2, 2009; and U.S. Pat. No. 6,945,933 titled INSTRUMENTS AND METHODS FOR MINIMALLY INVASIVE TISSUE RETRACTION AND SURGERY, filed Jun. 26, 2002 into this document by reference in its entirety.

FIELD

The present technology is generally related to medical devices to assist a surgeon during treatment of musculoskeletal disorders, and more particularly to a surgical system and method for accessing a surgical site to facilitate treatment. More particularly, the present disclosure is directed to a surgical retractor system including a plurality of primary blades and a plurality of supplemental blades that are each "modular" in that they can selectively be added to and removed from disclosed retractors.

BACKGROUND

Surgical retractors may be employed during a surgical treatment to provide access and visualization of a surgical site. Such retractors space apart and support tissue and/or other anatomical structures to expose anatomical structures at the surgical site and/or provide a surgical pathway for the surgeon to the surgical site. Conventional retractors may expand access to a tissue site using a limited number of blades that are typically fixed in number. A problem occurs when the limited number of blades are expanded, that tissue can creep into the surgical site between the blades. Although conventional retractors may articulate the limited number of blades, they often require multiple mechanical means for articulating each individual blade or at most a sub-group of blades. Conventional retractors typically are not generally capable of simultaneously expanding and/or simultaneously articulating a plurality of modular blades.

SUMMARY

The techniques of this disclosure generally relate to a modular retractor configured for use with a plurality of modular blades of varying types and sizes that is capable of expanding and/or articulating the plurality of modular blades simultaneously.

In one aspect, the present disclosure provides a modular retractor. The modular retractor may include a first annular retainer and a second annular retainer, the first annular retainer defining a first center point and the second annular retainer defining a second center point. The modular retractor may further include a central axis projecting through the first center point and the second center point. The modular retractor may further include a plurality of primary blades, the plurality of primary blades being coupled to the first annular retainer, each of the plurality of primary blades being configured to, selectively, pivotally couple to an adjacent primary blade of the plurality of primary blades. In some embodiments, the first annular retainer may be configured to, selectively, radially contract towards the first center point such that each of the plurality of primary blades articulates with respect to the central axis. In some embodiments, the second annular retainer may circumscribe the outside of the plurality of primary blades and be configured to apply a biasing force against each of the plurality of primary blades towards the central axis, for example.

In another aspect, the disclosure provides that each primary blade of the plurality of primary blades may be disposed around a circumference of the first annular retainer, for example.

In another aspect, the disclosure provides that each primary blade of the plurality of primary blades may be configured to, selectively, pivotally couple to the adjacent primary blade of the plurality of primary blades by a ball and socket mechanism, and the ball and socket mechanism may be configured to facilitate the articulation, for example.

In another aspect, the disclosure provides that each primary blade of the plurality of primary blades may include a corresponding primary blade retaining clip, and each primary blade retaining clip may be disposed at a top portion of each corresponding primary blade of the plurality of primary blades, for example.

In another aspect, the disclosure provides that in some embodiments, each primary blade retaining clip may include a first groove and a second groove. The first grooves of each primary blade retaining clip may define, together, a first pathway, and the second grooves of each primary blade retaining clip may define, together, a second pathway. In some embodiments, the first annular retainer may be operably coupled to each primary blade of the plurality of primary blades via the first pathway, and the second annular retainer may be operably coupled to each primary blade of the plurality of primary blades via the second pathway.

In another aspect, the disclosure provides that the first annular retainer, in a first mode of operation, is configured to radially contract within the first passageway and towards the first center point such that each of the plurality of primary blades articulates away from the central axis due to an applied radial force, and the first annular retainer, in a second mode of operation, is configured to release the applied radial force and return the primary blades to an initial position, for example.

In another aspect, the disclosure provides that, in some embodiments, the second annular retainer may apply the biasing force to the plurality of primary blades via the second pathway such that when the first annular retainer, in the second mode of operation, releases the applied radial force the biasing force facilitates the return of the primary blades to the initial position.

In another aspect, the disclosure provides that the modular retractor may further include at least one supplemental blade. In some embodiments, each supplemental blade of the at least one supplemental blades is configured to, selectively, pivotally couple to a pair of blades of the plurality of primary blades and the first annular retainer, and the first annular retainer is further configured to, selectively, radially contract towards the first center point such that each of the plurality of primary blades and each supplemental blade of the at least one supplemental blades articulates with respect to the central axis, for example Additionally, in some embodiments the second annular retainer may circumscribe the outside of the plurality of primary blades and each supplemental blade of the at least one supplemental blades, the second annular retainer may be further configured to apply a biasing force against each of the plurality of primary blades and each supplemental blade of the at least one supplemental blades towards the central axis.

In another aspect, the disclosure provides that, in some embodiments, each supplemental blade of the at least one supplemental blade includes a corresponding supplemental blade retaining clip, each supplemental blade retaining clip being disposed at a top portion of each supplemental blade of the at least one supplemental blade. Additionally, each supplemental blade retaining clip may include a first groove and a second groove, and each primary blade of the plurality of primary blades may include a corresponding primary blade retaining clip. Each primary blade retaining clip may be disposed at a top portion of each primary blade of the plurality of primary blades, and each primary blade retaining clip may include a first groove and a second groove, for example. Furthermore, in some embodiments, the first grooves of each supplemental blade retaining clip and the first grooves of each primary blade retaining clip may define, together, a first pathway, and the second grooves of each supplemental blade retaining clip and the second grooves of each primary blade retaining clip may define, together, a second pathway, for example. In some embodiments, the first annular retainer may be operably coupled to each supplemental blade of the at least one supplemental blades and each primary blade of the plurality of primary blades via the first pathway, and the second annular retainer is operably coupled to each supplemental blade of the at least one supplemental blades and each primary blade of the plurality of primary blades via the second pathway, for example.

In another aspect, the disclosure provides that, in some embodiments, each primary blade of the plurality of primary blades may include an outside surface, an inside surface opposite the outside surface, a first sidewall surface and a second sidewall surface opposite the first sidewall surface. Additionally, the first sidewall surface and the second sidewall surface may each extend between the outside surface and the inside surface, for example. In some embodiments, each first sidewall surface may include a first channel extending, at least partly, along the first sidewall surface, and each second sidewall surface may include a second channel extending, at least partly, along the second sidewall surface, for example.

In another aspect, the disclosure provides that each supplemental blade of the at least one supplemental blade includes an outside surface, an inside surface opposite the outside surface, a first sidewall surface and a second sidewall surface opposite the first sidewall surface. Additionally, the first sidewall surface and the second sidewall surface may each extend between the outside surface and the inside surface, for example. In some embodiments, each first sidewall surface may include a first protrusion projecting away from the first sidewall surface, and each second sidewall surface may include a second protrusion projecting away from the second sidewall surface.

In another aspect, the disclosure provides that each primary blade of the plurality of primary blades may include a first recess disposed on the corresponding first sidewall surface at an end portion of the corresponding first channel, and each primary blade of the plurality of primary blades may include a second recess disposed on the corresponding second sidewall surface at an end portion of the corresponding second channel, for example.

In another aspect, the disclosure provides that, in some embodiments, each first protrusion may be configured to engage, selectively, with a corresponding first recess, and each second protrusion is configured to engage, selectively, with a corresponding second recess, for example.

In another aspect, the disclosure provides that the modular retractor may further include a handle and a contraction mechanism operably coupled to the first annular retainer. The contraction mechanism may be configured to cause radial contraction of the first annular retainer by pulling at least one end portion of the first annular retainer within a cavity of the handle.

In another aspect, the disclosure provides that, in some embodiments, the contraction mechanism includes: a sliding actuator, a turnbuckle, and/or a set screw and a sliding ring, for example.

In another aspect, the disclosure provides a modular retractor system. The system may include a first annular retainer and a second annular retainer, the first annular retainer may define a first center point and the second annular retainer may define a second center point, for example Additionally, the system may define a central axis projecting through the first center point and the second center point. Furthermore, the system may include a plurality of primary blades, the plurality of primary blades may be coupled to the first annular retainer, each of the plurality of primary blades may be configured to, selectively, pivotally couple to an adjacent primary blade of the plurality of primary blades, for example. The system may further include a plurality of supplemental blades, each supplemental blade of the plurality of supplemental blades may be configured to, selectively, in an installed position, pivotally couple to a pair of adjacent primary blades of the plurality of primary blades and the first annular retainer, for example. In some embodiments, the first annular retainer may be configured to, selectively, radially contract towards the first center point such that each of the plurality of primary blades articulates with respect to the central axis and each supplemental blade of the plurality of supplemental blades, in the installed position, articulates with respect to the central axis, for example. In some embodiments, the second annular retainer circumscribes the outside of the plurality of primary blades and the outside of each supplemental blade of the plurality of supplemental blades in the installed position, and the second annular retainer may be configured to apply a biasing force against each of the plurality of primary blades and each supplemental blade of the plurality of supplemental blades, in the installed position, towards the central axis, for example.

In another aspect, the disclosure provides that, in some embodiments, each supplemental blade of the plurality of supplemental blades includes a corresponding supplemental blade retaining clip. Additionally, each supplemental blade retaining clip may be disposed at a top portion of each supplemental blade of the plurality of supplemental blades, and each supplemental blade retaining clip may include a first groove and a second groove, for example. In some embodiments, each primary blade of the plurality of primary blades may include a corresponding primary blade retaining clip, each primary blade retaining clip may be disposed at a top portion of each primary blade of the plurality of primary blades, and each primary blade retaining clip comprises a first groove and a second groove, for example. Additionally, the first grooves of each supplemental blade retaining clip and the first grooves of each primary blade retaining clip may define, together, a first pathway, and the second grooves of each primary blade retaining clip may define, together, a second pathway. In some embodiments, the first annular retainer may be operably coupled to each supplemental blade of the at least one supplemental blades and each primary blade of the plurality of primary blades via the first pathway, and the second annular retainer may be operably coupled to each supplemental blade of the at least one supplemental blades and each primary blade of the plurality of primary blades via the second pathway, for example.

In another aspect, the disclosure provides that, in some embodiments, each primary blade of the plurality of primary blades includes a first outside surface, a first inside surface opposite the first outside surface, a first sidewall surface and a second sidewall surface opposite the first sidewall surface, and the first sidewall surface and the second sidewall surface may each extend between the outside surface and the inside surface, for example. In some embodiments, each supplemental blade of the plurality of supplemental blades may include a second outside surface, and a second inside surface opposite the outside surface, a third sidewall surface and a fourth sidewall surface opposite the third sidewall surface, the third sidewall surface and the fourth sidewall surface may each extend between the second outside surface and the second inside surface, for example. In some embodiments, each first sidewall surface of each primary blade may include a first channel extending, at least partly, along the first sidewall surface of the corresponding primary blade, and each second sidewall surface of each primary blade may include a second channel extending, at least partly, along the second sidewall surface of the corresponding primary blade, for example. In some embodiments, each third sidewall surface of each supplemental blade may include a first protrusion projecting away from the third sidewall surface, and each fourth sidewall surface of each supplemental blade may include a second protrusion projecting away from the fourth sidewall surface.

In another aspect, the disclosure provides that, in some embodiments, each primary blade of the plurality of primary blades may include a first recess disposed on the corresponding first sidewall surface at an end portion of the corresponding first channel, and each primary blade of the plurality of primary blades may include a second recess disposed on the corresponding second sidewall surface at an end portion of the corresponding second channel, for example.

In another aspect, the disclosure provides that each first protrusion may be configured to engage, selectively, with a corresponding first recess, and each second protrusion may be configured to engage, selectively, with a corresponding second recess, for example.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 5A is a perspective view of a modular retractor system.

FIG. 5B is a top view of a modular retractor system.

FIG. 6A is a perspective view of a modular retractor system being moved into an open position.

FIG. 6B is a top view of a modular retractor system including an actuator being moved into the open position.

FIG. 8A is a perspective view of a modular retractor system including a supplemental blade being moved into an installed position.

FIG. 8B is a top down view of a modular retractor system including a supplemental blade being moved into an installed position.

FIG. 9A is a perspective view of a modular retractor system including a supplemental blade being moved into an installed position.

FIG. 9B is a top down view of a modular retractor system including a supplemental blade being moved into an installed position.

FIG. 10A is a perspective view of a modular retractor system including a supplemental blade fully inserted in the installed position.

FIG. 10B is a top down view of a modular retractor system including a supplemental blade fully inserted in the installed position.

FIG. 11a is a perspective view of a modular retractor system including a plurality of primary blades and a supplemental blade being articulated into an open position.

FIG. 11b is a top down view of a modular retractor system including a plurality of primary blades and a supplemental blade being articulated into an open position.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Figure 1:
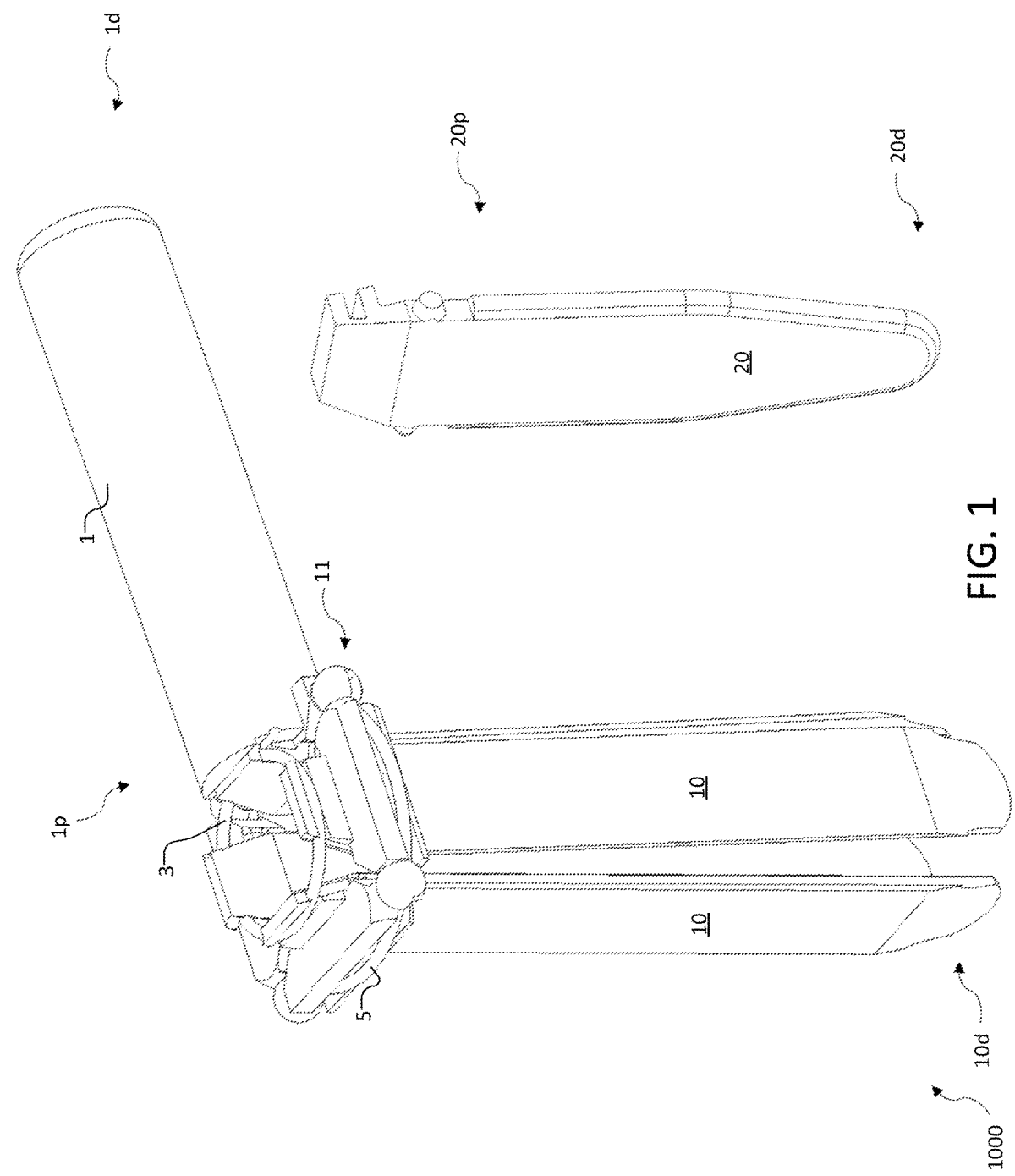
FIG. 1 is a perspective view of a modular retractor system including a plurality of installed primary blades and a supplemental blade.

Referring generally to FIGS. 1A-15B a modular retractor system 1000 is disclosed. FIG. 1 is an example perspective view of a modular retractor system 1000 including a plurality of installed primary blades 10 and a non-installed supplemental blade 20. As used in this specification and the appended claims, the term "modular" shall have its ordinary technical meaning, referring to components that can be independently created, modified, replaced or exchanged with disclosed systems and components thereof. For example, both of the primary blades 10 and secondary blades 20 may each be independently replaced, exchanged, and/or added for use with the disclosed modular retractor system.

The modular retractor system 1000 may include a handle 1 that is operably coupled to a first annular retaining ring 3 and a second annular retaining ring 5, for example. In some embodiments, each primary blade 10 is disposed around a circumference of the first annular retaining ring 3. The first annular retaining ring 3 may be disposed above the second annular retaining ring 5. The supplemental blade 20 is illustrated in a non-installed position. However, supplemental blade 20 may be installed for use with modular retractor system 1000, as will be explained in further detail below.

Figure 2:
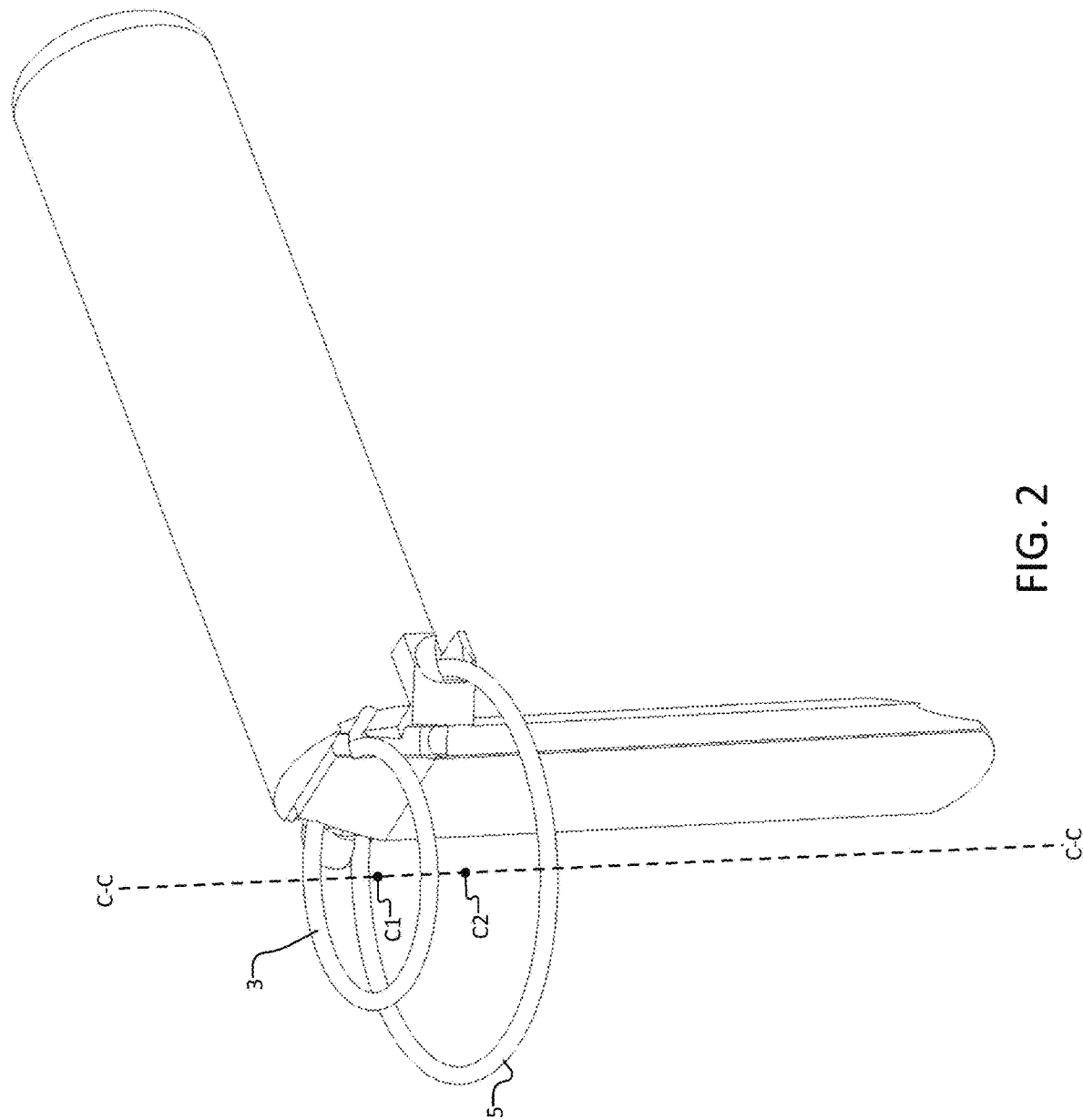
FIG. 2 is a perspective view of a modular retractor system including a first annular retaining ring and a second annular retaining ring.

FIG. 2 is an example perspective view of a modular retractor system 1000 including a first annular retaining ring 3 and a second annular retaining ring 5. The first annular retaining ring 3 may be oriented into a substantially circular arrangement defining a first center point C1. Similarly, the second annular retaining ring 5 may be oriented into a substantially circular arrangement defining a second center point C2. Annular retaining rings, 3, 5 may be formed of a deformable material, such as, for example, a flexible wire, such as nitinol or the like, a flexible plastic, a relatively thin metallic wire or the like, and/or a combination of the above disclosed materials. In some embodiments, annular retaining ring 3 may have a substantially circular cross-section and in other embodiments, annular retaining ring 3 may resemble a ribbon or flat chord. In some embodiments, annular retaining ring 3 may be formed of a different material than annular retaining ring 5. In the illustrated embodiment, the first center point C1 and second center point C2 may define an axis C-C, for example. Axis C-C may be oriented substantially vertical with respect to handle 1 of modular retractor system 1000.

Figure 3B:
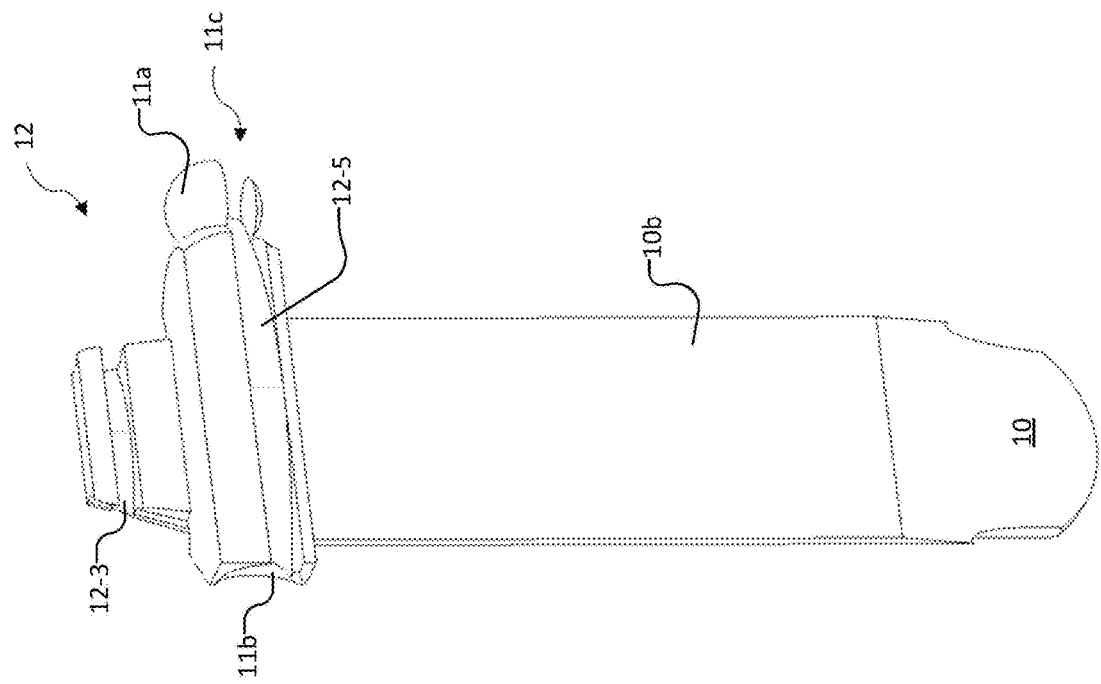
FIG. 3B is a perspective view of an outside surface of a primary blade.
Figure 3A:
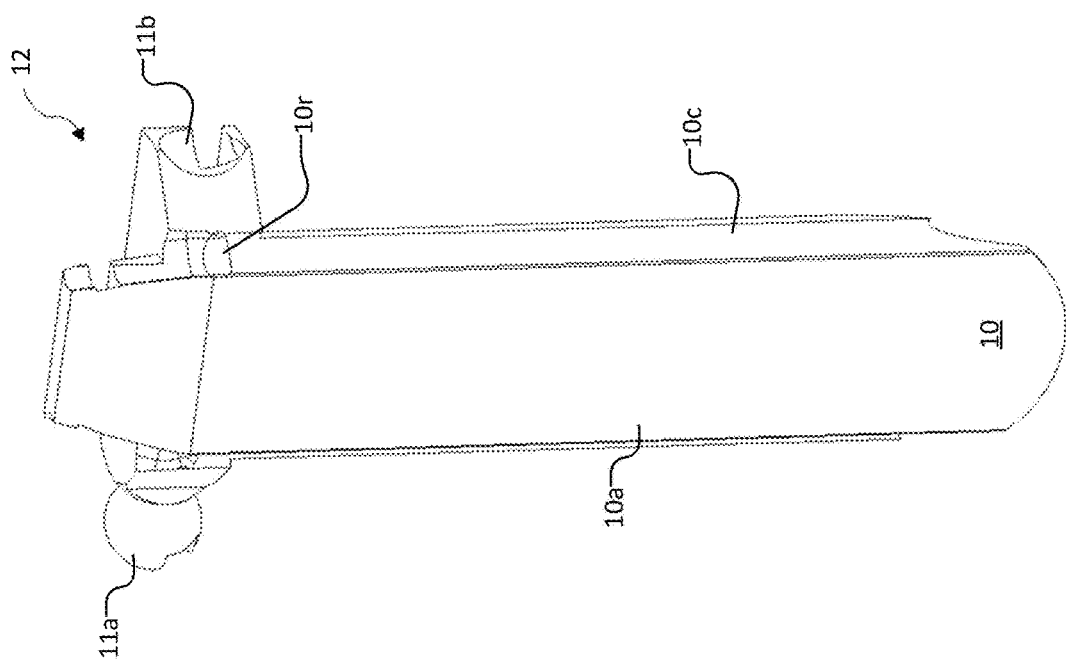
FIG. 3A is a perspective view of an inside surface of a primary blade.

FIG. 3A is an example perspective view of an inside surface 10a of a primary blade 10. FIG. 3B is an example perspective view of an outside surface 10b of a blade. Primary blade 10 may include channel 10c extending down side surfaces thereof. Although primary blade 10 is illustrated as including a planar outside surface 10a and a planar inside surface 10b it shall be understood that the illustrations are an example and the inventive concepts disclosed herein are not limited to blades having flat or planar surfaces. For example, in other embodiments, primary blade 10 may include curved surfaces defined by a radius of a circle or curved surfaces that are defined by a segment of an ellipsis. For example still, in at least one embodiment, surfaces 10a, 10b may be shaped like a segment of an oval cylinder. In at least one embodiment, surfaces 10a, 10b may be shaped in such a way as to correspond to the shape of a set of nested dilators such as, for example, the dilators referred to in U.S. Pat. No. 7,976,463. For example, the surfaces 10a, 10b may correspond to the shape of and fit around a last dilator of one or more sequential dilators. In use, an end user may place the primary blades 10 around the last dilator in a closed position for insertion into an opening of a surgical site. Thereafter, an end user may enlarge the opening of the surgical site in a manner as will be explained in further detail below.

Primary blade 10 may include a primary blade retaining clip 12 disposed at a top portion thereof, for example. In some embodiments, primary blade retaining clip 12 may include a first groove 12-3 at an upper portion thereof and a second groove 12-5 disposed directly beneath and proximate to the first groove 12-3. First groove 12-3 may be configured to snap to first annular retaining ring 3. For example, first groove 12-3 and annular retaining ring 3 may be deformable, at least partly, and be sized to snap together. The first groove 12-3 may be curved and include a cross sectional depth corresponding to a radius of curvature of the first annular retaining ring 3. At least one advantage of using a snapping ring as the annular retaining ring 3 is that modular retractor system 1000 can accommodate various amounts of primary blades 10, e.g., 2, 3, 4, 5, 6, etc. Additionally, first annular retaining ring 3 and first groove 12-3 may comprise low friction surfaces that may facilitate the sliding of annular retaining ring 3 within first groove 12-3, as will be explained in more detail below.

Second groove 12-5 may be configured to snap to second annular retaining ring 5. For example, second groove 12-5 and annular retaining ring 5 may be deformable, at least partly, and be sized to snap together. The first groove 12-3 may be curved and include a cross sectional depth corresponding to a radius of curvature of the first annular retaining ring 3. In other embodiments, second annular retaining ring 5 may not snap to second groove 12-5 and be passively retaining within second groove 12-5. For example, in some embodiments, second annular retaining ring 5 may comprise an elastic ribbon that when seated within second groove 12-5 is retaining within the groove due to a biasing force.

In disclosed embodiments, the first grooves 12-3 of each primary blade retaining clip 12 may define, together, a first pathway, and the second grooves 12-5 of each primary blade retaining clip 12 may define together, a second pathway. Additionally, the first annular retainer 3 may be operably coupled to each primary blade 10 via the first pathway, and the second annular retainer 5 may be operably coupled to each primary blade 10 via the second pathway, for example.

Primary blade 10 may further include a ball and socket mechanism 11 including a ball portion 11a and a corresponding socket portion 11b. For example, each primary blade 10 may include a ball portion 11a on a first side surface and a corresponding socket portion 11b on a second side surface opposite the first side surface. Disclosed ball and socket mechanism 11 may be configured to allow second annular retaining ring 5 to pass through an internal channel 11e. In practice, a first primary blade 10 and a second primary blade 10 may be operably coupled at a junction including a ball portion 11a from the first primary blade 10 and a corresponding socket portion 11b of the second blade.

Figure 4B:
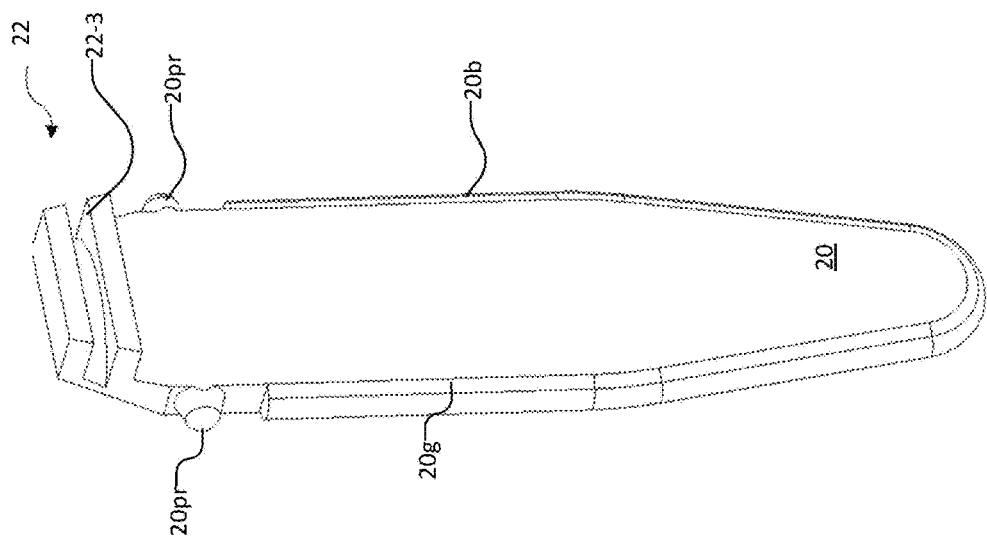
FIG. 4B is a perspective view of an outside surface of a supplemental blade.
Figure 4A:
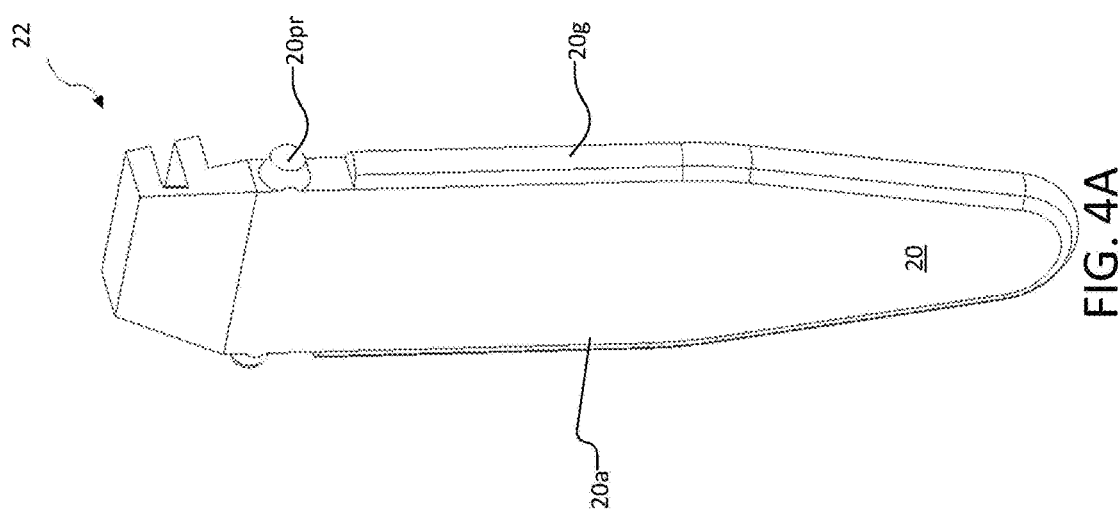
FIG. 4A is a perspective view of an inside surface of a supplemental blade.

FIG. 4A is an example perspective view of an inside surface 20a of a supplemental blade 20. FIG. 4B is an example perspective view of an outside surface 20b of a supplemental blade 20. Although supplemental blade 20 is illustrated as including a planar outside surface 20a and a planar inside surface 20b it shall be understood that the illustrations are an example and the inventive concepts disclosed herein are not limited to blades having flat or planar surfaces. For example, in other embodiments, supplemental blade 20 may include curved surfaces defined by a radius of a circle or curved surfaces that are defined by a segment of an ellipse. For example still, in at least one embodiment, surfaces 20a, 20b may be shaped like a segment of an oval cylinder.

In some embodiments, supplemental blade 20 may include a groove 20g on side surfaces thereof. Groove 20g may resemble a semi-circle in cross section, for example Groove 20g may extend down along a portion of side surfaces of supplemental blade 20. Groove 20g may be configured to operably slide in and nest with channel 10c, as will be explained in further detail below. Supplemental blade 20 may further include a protrusion 20pr extending laterally and away from side surfaces of supplemental blade 20, for example. Protrusion 20pr may be disposed proximate to and above groove 20g. Protrusion 20pr may have a generally conical shape with a flat surface at an outermost portion thereof. Supplemental blade 20 may include a supplemental blade retaining clip 22. In disclosed embodiments, supplemental blade retaining clip 22 may be the same as, similar, or substantially the same as primary blade retaining clip 12. In the illustrated embodiment, supplemental blade retaining clip 22 may include a groove 20-3. The flat surface of protrusion 20pr may be a planar surface that extends laterally and farther out from supplemental blade 20 than groove 20-3. Protrusion 20pr may be configured to nest inside of recess 10r of primary blade 10, as will be explained in further detail below.

Groove 20-3 may be configured to snap to and/or couple with first annular retaining ring 3. For example, groove 20-3 and annular retaining ring 3 may be deformable, at least partly, and be sized to snap together. The groove 20-3 may be curved and include a cross sectional depth corresponding to a radius of curvature of the first annular retaining ring 3. At least one advantage of using a snapping ring as the annular retaining ring 3 is that modular retractor system 1000 can accommodate various amounts of primary blades 10 and/or supplemental blades 20, e.g., 2, 3, 4, 5, 6, etc. of each type of blade, for example. Additionally, first annular retaining ring 3 and groove 20-3 may comprise low friction surfaces that may facilitate the sliding of annular retaining ring 3 within groove 20-3, as will be explained in more detail below.

FIG. 5A is an example perspective view of a modular retractor system 1000 including a plurality of installed primary blades 10. FIG. 5B is an example top view of a modular retractor system 1000 of FIG. 5A. In the example embodiment, primary blades 10 are operably and pivotally coupled by ball and socket mechanism 11. Additionally, primary blades 10 may be urged inward toward axis C-C due to a biasing force applied to primary blades 10 by second annular retaining ring 5. For example, second annular retaining ring 5 may be an elastic material or a semi-elastic material exerting a natural biasing force against primary blades 10 urging them towards axis C-C. In the illustrated embodiment, modular retractor system 1000 is in a contracted position.

FIG. 6A is an example perspective view of a modular retractor system 1000 being moved into an open position. FIG. 6B is an example top view of a modular retractor system 1000 including an expansion mechanism comprising an actuator 1a moving the primary blades 10 into the open position. Actuator 1a may be a slidable actuator that is coupled to a first end portion 3y and a second end portion 3z of first annular retaining ring 3 that extend into a cavity within handle 1. In practice, an end user may slide actuator 1a towards a distal side 1d of handle 1 (illustrated schematically by arrows). In this way, actuator 1a may apply a tension force to first and second end portions 3y, 3z of first annular retaining ring 3 such that first annular retaining ring 3 contracts inward radially towards axis C-C. For example, actuator 1a may be configured to cause first annular retaining ring 3 to contract radially inward, or at least urge primary blades 10 to contract inward towards axis C-C via direct contact at first groove 12-3. Stated another way, first annular retaining ring 3 may apply a force to primary blades 10 at a top portion thereof in a direction extending towards axis C-C. In turn, the applied force from first annular retaining ring 3 at first groove 12-3 of primary blade retaining clip 12 may cause primary blades 10 to pivot outwardly at a distal end 10d (shown by arrows). In the disclosed embodiment, each of primary blades 10 may articulate outwardly at a distal end 10d with respect to axis C-C. The articulation may increase the size of an opening of a surgical site.

In some embodiments, first annular ring 3 may be operable via a contraction mechanism comprising a turnbuckle and/or a set screw and a sliding ring (not illustrated) and a suitable actuator. For example, a turnbuckle may be disposed medially within handle 1 and operably coupled to end portions 3y, 3z near the distal side of handle 1 and a turning knob disposed near the proximate side of handle 1, for example. An end user may turn the turning knob and cause a rotation of the turnbuckle that applies a tensile force to end portions 3y, and 3z, for example. Similarly, a set screw may be disposed medially within handle 1 and operably coupled to end portions 3y, 3z by a sliding ring near the distal side of handle 1, for example. The sliding ring may slide longitudinally along the length of the set screw forward and backward upon turning the set screw, for example. In at least one embodiment, the set screw is rotatable via a turning knob or driving portion disposed at the distal side of handle 1, for example. The driving portion may be rotatable via an external tool such as a screwdriver or the like, for example.

Figure 7B:
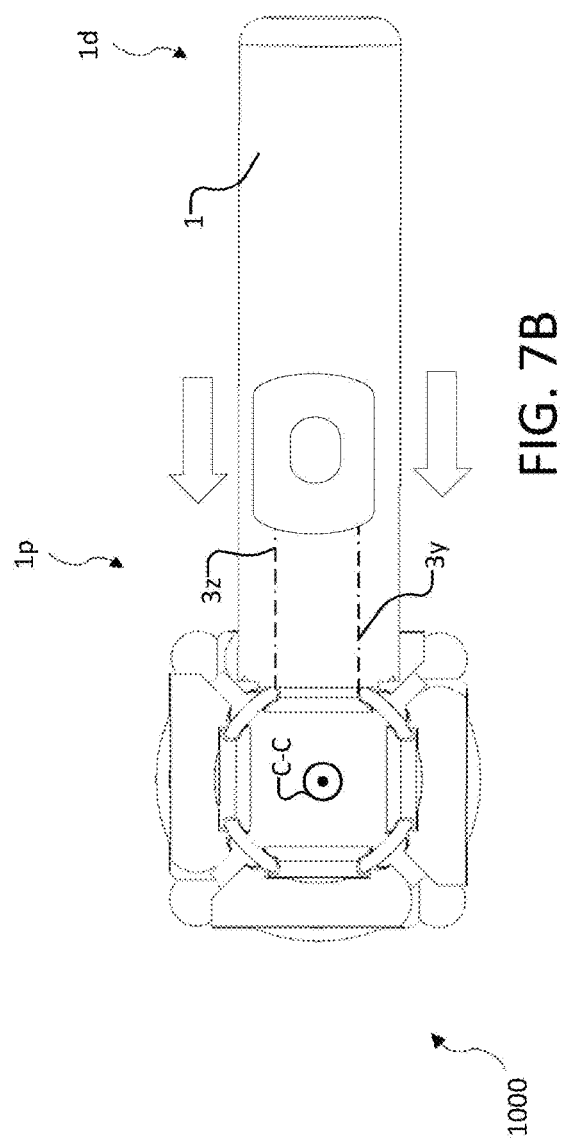
FIG. 7B is a top view of a modular retractor system including an actuator being moved into the closed position.
Figure 7A:
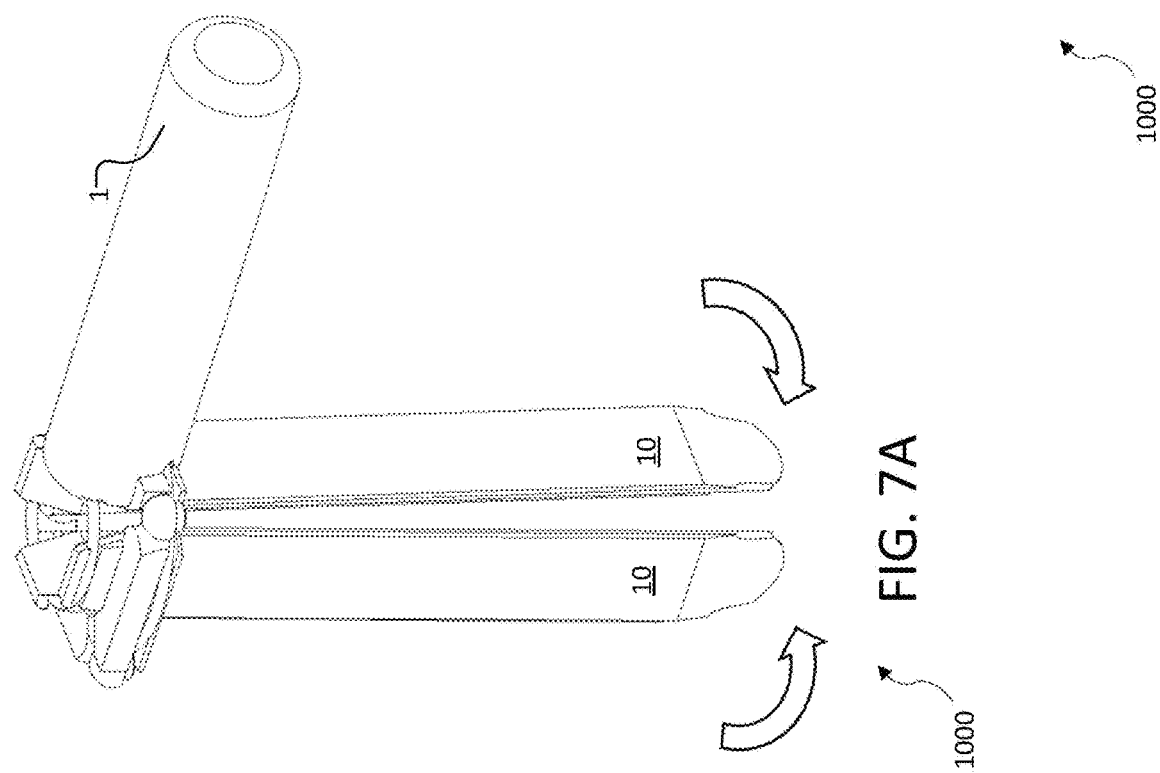
FIG. 7A is a perspective view of a modular retractor system being moved into a closed position.

FIG. 7A is an example perspective view of a modular retractor system 1000 being moved into a closed position. FIG. 7B is an example top view of a modular retractor system 1000 including an actuator 1a being moved into the closed position. When actuator 1a is moved towards the proximal side 1p of handle, the tension force applied to first and second end portions 3y, 3z of first annular retaining ring 3 is released such that first annular retaining ring 3 expands outward and away from axis C-C. For example, actuator 1a may be configured to cause first annular retaining ring 3 to expand, at least partly, such that an internal radial force towards axis C-C is no longer applied to primary blades 10 by first annular retaining ring 3. In some embodiments, expanding first annular retaining ring 3 radially away from axis C-C urges the distal portion 10d of primary blades 10 to articulate inwards towards axis C-C Additionally and/or alternatively, second annular retaining ring 5 may apply a biasing force against supplemental primary blades 10 such that supplemental primary blades 10 pivot at ball and socket mechanism 11. The biasing force applied by second annular ring 5 may urge the distal portion 10d of primary blades 10 to articulate inwards towards axis C-C.

FIG. 8A is an example perspective view of a modular retractor system 1000 including a supplemental blade 20 being moved into an installed position. FIG. 8B is an example top down view of a modular retractor system 1000 including a supplemental blade being moved into an installed position. In the illustrated embodiment, a first supplemental blade 20 may be positioned between an adjacent pair primary blades 10, for example. As previously explained, supplemental blade 20 may include a groove 20g extending along side surfaces thereof. Groove 20g may be configured to mate with a corresponding channel 10c extending along side surfaces of primary blade 10, for example. In the illustrated embodiment, supplemental blade 20 includes a groove 20g that extends from a proximal portion 20p of supplemental blade 20 to the distal portion 20d of supplemental blade 20. For example, in the illustrated embodiment, groove 20g extends along a first side surface of supplemental blade 20 all the way down to the distal portion 20d and groove 20g extends along a second side surface of supplemental blade 20 all the way down to the distal portion 20p. As shown in FIG. 9A, the distal portion 20d is placed between adjacent primary blades 10 and the groove 20g is mated with the corresponding channels 10c.

FIG. 9A is an example perspective view of a modular retractor system 1000 including a supplemental blade 20 being moved into an installed position. FIG. 9B is an example top down view of a modular retractor system including a supplemental blade being moved into an installed position. In practice, an end user may insert the distal portion 20d of supplemental blade 20 between two adjacent primary blades 10 such that the groove 20g at the narrowed tip of the distal portion 20d mates with corresponding channels 10c of supplemental primary blade 10, for example, an end user may apply a downward force to supplemental blade 20 while supplemental blade 20 is guided into position between adjacent primary blades 10. In pushing supplemental blade 20 downward, the adjacent primary blades 10 may separate at the ball and socket mechanism 11. Additionally, the first annular retaining ring 3 may expand, at least partly, to accommodate supplemental blade 20. For example, the first annular retaining ring 3 may expand radially away from axis C-C.

FIG. 10A is an example perspective view of a modular retractor system 1000 including a supplemental blade 20 fully inserted in the installed position. FIG. 10B is an example top down view of a modular retractor system 1000 including a supplemental blade 20 fully inserted in the installed position. In the illustrated embodiment, supplemental blade 20 has been fully inserted into an installed position where protrusions 20pr are mated inside of corresponding recesses 10r of primary blades 10. In practice, an end user may slide supplemental blade 20 downward with the guiding assistance of grooves 20g and channels 10c until protrusions 20pr come into alignment with corresponding recesses 10r. In seating supplemental blade 20 between a pair of adjacent primary blades 10, the protrusions 20pr and corresponding recesses 10r may function as a pivoting point. Additionally, supplemental blade 20 may be operably coupled with first annular retaining ring 3 at groove 22-3. For example, first retaining ring 3 may extend through groove 22-3 consistent with previous disclosure.

In practice, by inserting and pushing supplemental blade 20 into the installed position an opening of a surgical access site may be enlarged without requiring an articulation of the primary and supplemental blades 10, 20. Thereafter, the primary and supplemental blades 10, 20 may be selectively articulated in varying degree to enlarge the opening of the surgical access site as may be desired, for example. In some embodiments, supplemental blades 20 may be added to modular retractor system 1000 in advance of being placed in an opening of a surgical site. For example, both primary blades 10 and supplemental blades 20 may be selectively added to modular retractor system 1000 and then be placed around a set of nested dilators, or at least an outermost dilator, such as, for example, the dilators referred to in U.S. Pat. No. 7,976,463. Thereafter, the nested dilators may be removed and an end user may articulate both the primary blades 10 and supplemental blades 20 to enlarge an opening of the surgical access site as may be desired, for example.

FIG. 11a is an example perspective view of a modular retractor system 1000 including a plurality of primary blades 10 and a supplemental blade 20 being articulated into an open position. FIG. 11b is an example top down view of a modular retractor system 1000 including a plurality of blades 20 and a supplemental blade 20 being articulated into an open position. Consistent with previous disclosure, an end user may cause first annular retaining ring 3 to contract inward radially and exert a circumferential force at grooves 12-3 and 22-3. The applied radial force may cause primary blades 10 and supplemental blades 20 to pivot with respect to one another and axis C-C because of the corresponding ball and socket mechanisms 11 and the pivoting junction between protrusions 20pr of supplemental blades 20 and corresponding recesses 10r of primary blades 10. As illustrated, the distal ends of primary blades 10 and supplemental blades 20 articulate outwardly. In doing so, a surgeon may expand a surgical access site.

Figure 12A:
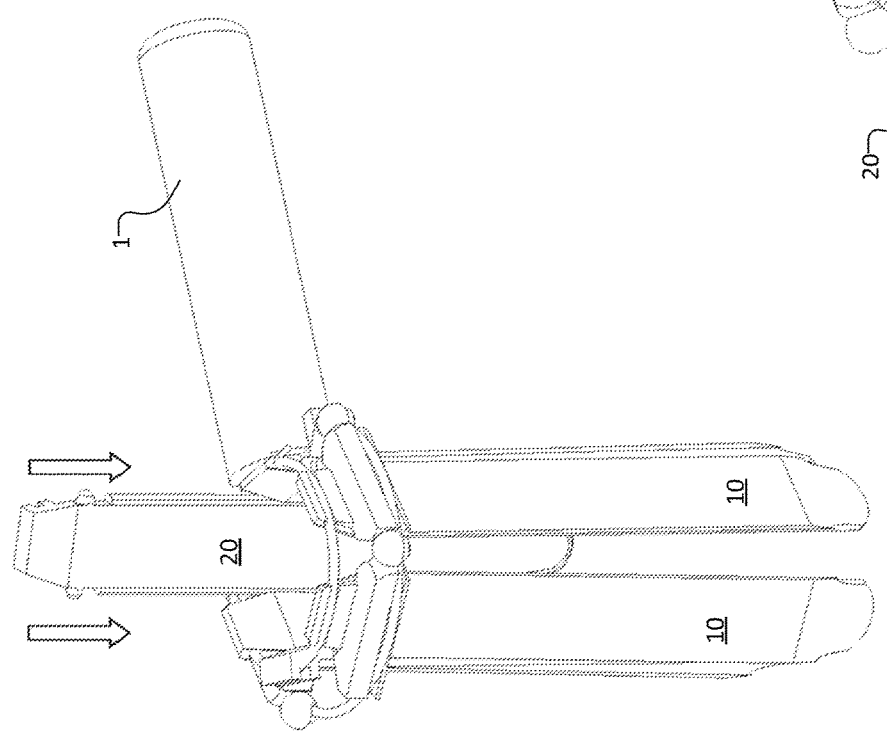
FIG. 12A is a perspective view of a modular retractor system including a plurality of primary blades, a first supplemental blade in the installed position, and a second supplemental blade being inserted into an installed position.
Figure 12B:
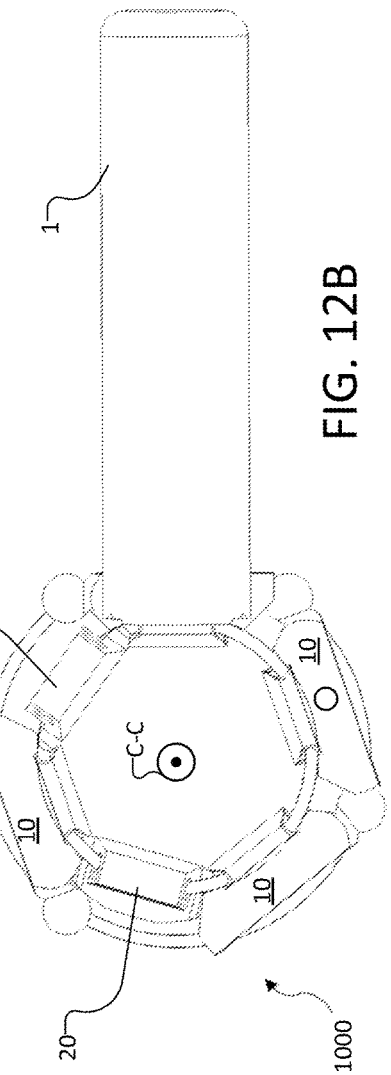
FIG. 12B is a top down view of a modular retractor system including a plurality of primary blades, a first supplemental blade in the installed position, and a second supplemental blade being inserted into an installed position.

FIG. 12A is an example perspective view of a modular retractor system 1000 including a plurality of primary blades 10, a first supplemental blade 20 in the installed position, and a second supplemental blade 20 being inserted into an installed position. FIG. 12B is an example top down view of a modular retractor system 1000 including a plurality of primary blades 10, a first supplemental blade 20 in the installed position, and a second supplemental blade 20 being inserted into an installed position. Consistent with the above disclosure, a second supplemental blade 20 may be inserted and installed via groove 20g and channels 10c in substantially the same manner as explained above.

Figure 13A:
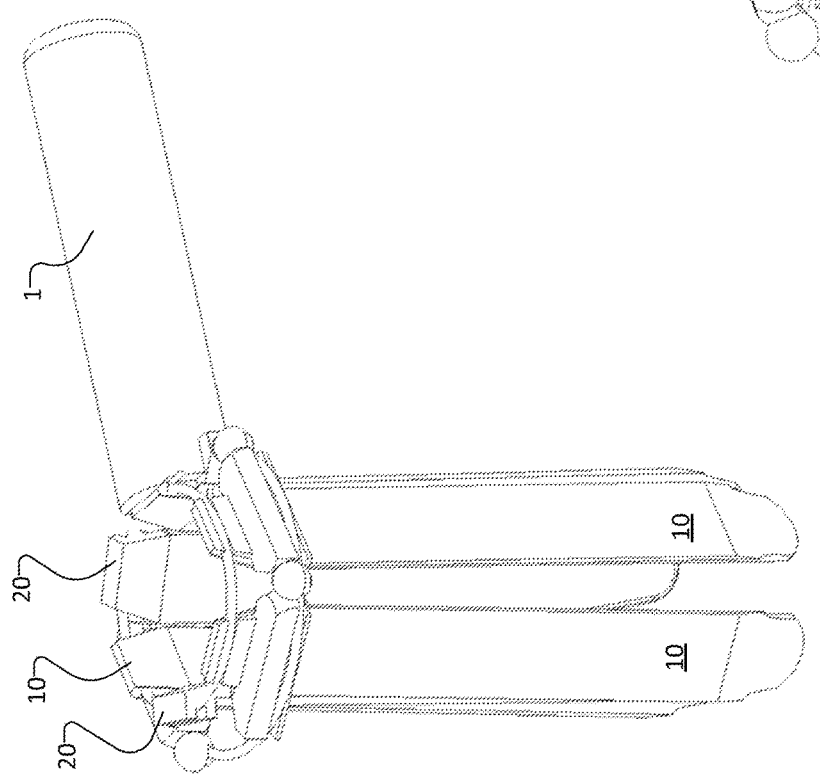
FIG. 13A is a perspective view of a modular retractor system including a plurality of primary blades, a first supplemental blade in the installed position, and a second supplemental blade in the installed position.
Figure 13B:
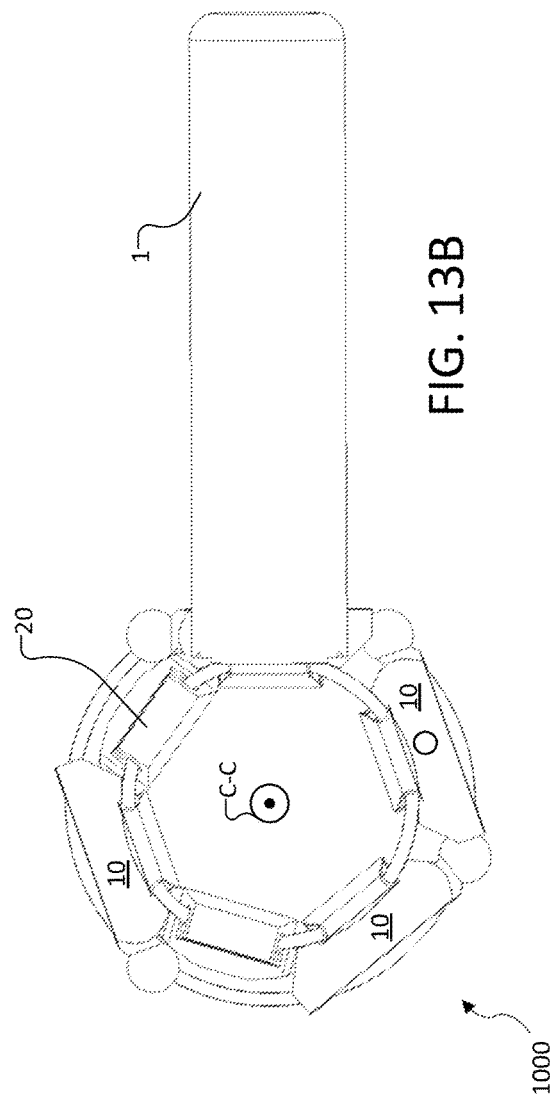
FIG. 13B is a top down view of a modular retractor system including a plurality of primary blades, a first supplemental blade in the installed position, and a second supplemental blade in the installed position.

FIG. 13A is an example perspective view of a modular retractor system 1000 including a plurality of primary blades 10, a first supplemental blade 20 in the installed position, and a second supplemental blade 20 in the installed position. FIG. 13B is an example top down view of a modular retractor system 1000 including a plurality of primary blades 10, a first supplemental blade 20 in the installed position, and a second supplemental blade 20 in the installed position. Consistent with the previous disclosure, by inserting the second supplemental blade 20 into the installed position, the first annular retaining ring 3 may expand radially outwardly to accommodate the second supplemental blade 20. Additionally, the second supplemental blade 20 may be pivotally coupled with a pair of adjacent primary blades 10 in substantially the same manner as explained above. The process may be repeated to accommodate any number of blades as may be desired or necessary for each unique surgery being performed.

Figure 14B:
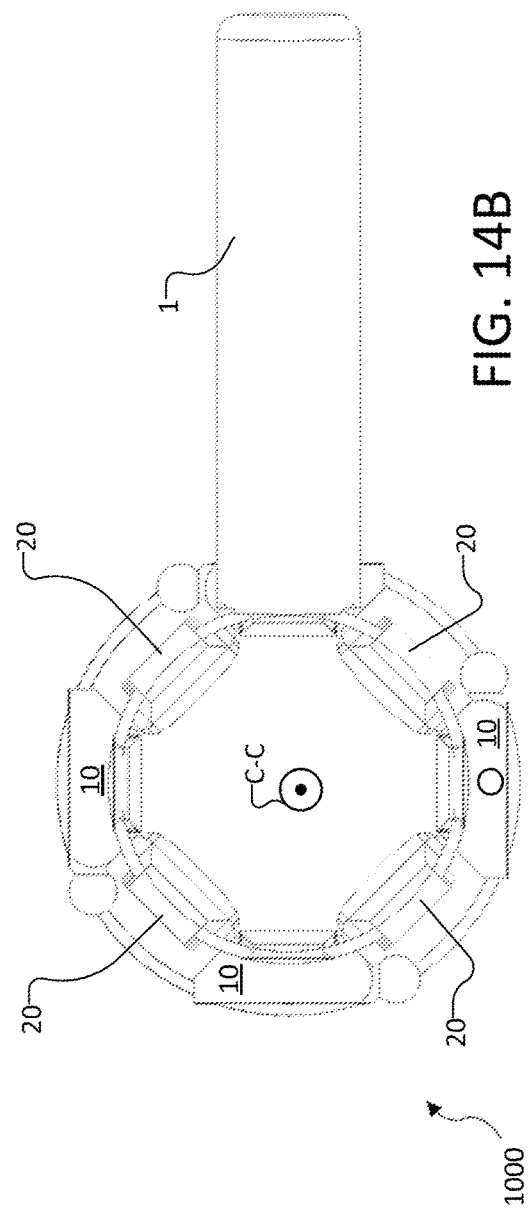
FIG. 14B is a top down view of a modular retractor system including a plurality of primary blades, and a plurality of supplemental blades in the installed position.
Figure 14A:
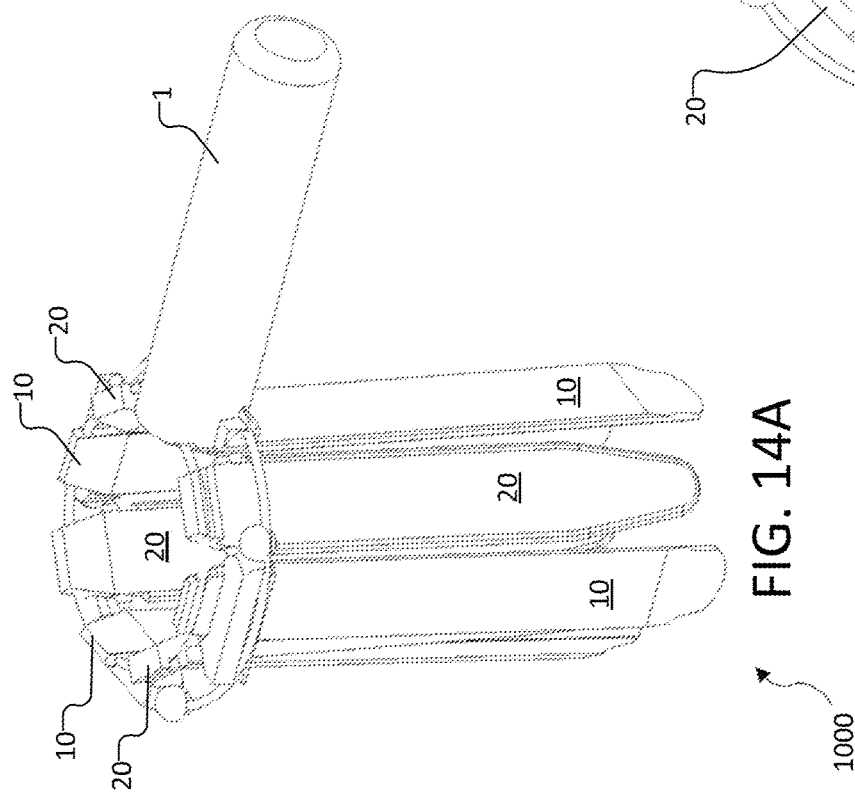
FIG. 14A is a perspective view of a modular retractor system including a plurality of primary blades, and a plurality of supplemental blades in the installed position.

FIG. 14A is an example perspective view of a modular retractor system 1000 including a plurality of primary blades 10, and a plurality of supplemental blades 20 in the installed position. FIG. 14B is an example top down view of a modular retractor system 1000 including a plurality of primary blades 10, and a plurality of supplemental blades 20 in the installed position. In the example embodiment, four primary blades 10 and four supplemental blades 20 are operably and pivotally coupled together at each respective pivoting junction where each protrusion 20pr is mated with a corresponding recess 10r. Additionally the four primary blades 10 and four supplemental blades 20 are operably coupled to first annular retaining ring 3. In the disclosed embodiment, due to the number of primary blades 10 and supplemental blades 20, a distance from an edge portion of annular retaining ring 3 to axis C-C is relatively greater than in embodiments having less primary blades 10 and/or supplemental blades 20.

Figure 15A:
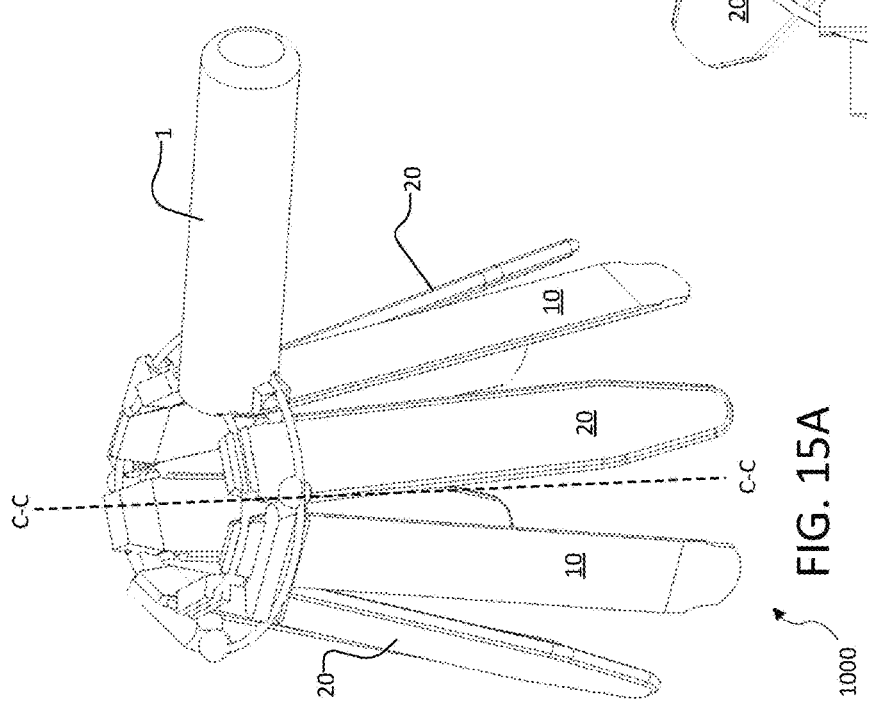
FIG. 15A is a perspective view of a modular retractor system including a plurality of primary blades and a plurality of supplemental blades in the installed position being articulated into an open position.
Figure 15B:
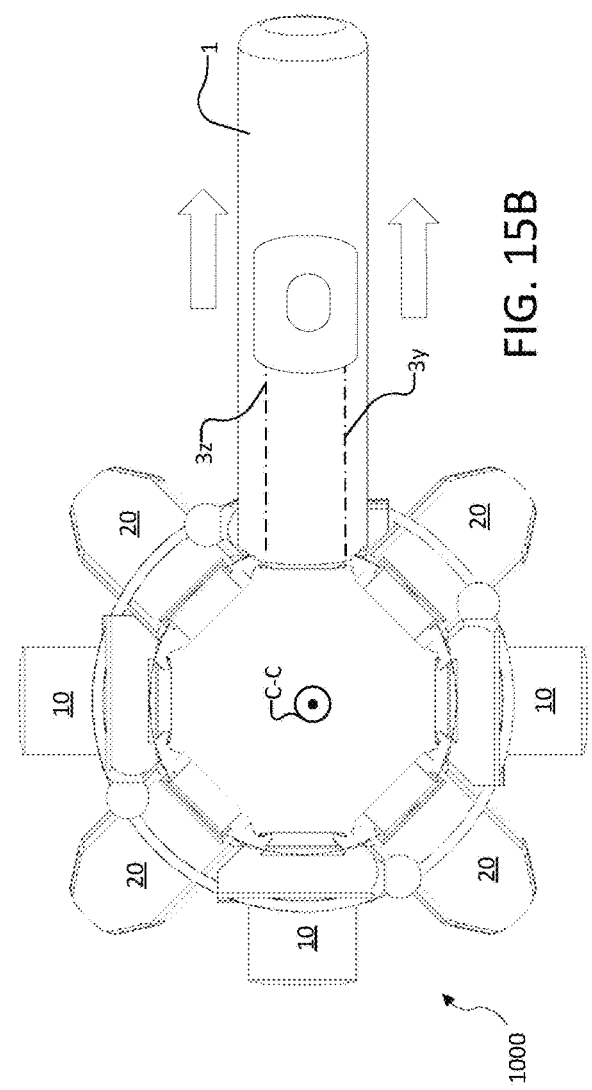
FIG. 15B is a top down view of a modular retractor system including a plurality of primary blades, and a plurality of supplemental blades in the installed position being articulated into the open position.

FIG. 15A is an example perspective view of a modular retractor system 1000 including a plurality of primary blades 10 and a plurality of supplemental blades 20 in the installed position being articulated into an open position. FIG. 15B is an example top down view of a modular retractor system 12-3 including a plurality of primary blades 10, and a plurality of supplemental blades 20 in the installed position being articulated into the open position. Consistent with previous disclosure, an end user may toggle an actuator 1a by sliding the actuator 1a towards a proximal portion 1a of handle 1. In doing so, first annular retaining ring 3 may apply a radial force against grooves 12-3 of primary blades 10 and grooves 22-3 of supplemental blades 20. The applied radial force may consequently cause the distal end portions 10d of primary blades 10 and the distal end portions of blades 20 to articulate away from central axis C-C.

What is claimed is:

1. A modular retractor, comprising:
a handle;
a first annular retainer and a second annular retainer, the first annular retainer defining a first center point and the second annular retainer defining a second center point;
a central axis projecting through the first center point and the second center point;
a plurality of primary blades, the plurality of primary blades being coupled to the first annular retainer, each primary blade of the plurality of primary blades being configured to, selectively, pivotally couple to an adjacent primary blade of the plurality of primary blades;
a contraction mechanism operably coupled to the first annular retainer, the contraction mechanism being configured to cause radial contraction of the first annular retainer by pulling at least one end portion of the first annular retainer within a cavity of the handle;
wherein the first annular retainer is configured to, selectively, radially contract towards the first center point such that each primary blade of the plurality of primary blades articulates with respect to the central axis; and
wherein the second annular retainer circumscribes the outside of the plurality of primary blades and is configured to apply a biasing force against each primary blade of the plurality of primary blades towards the central axis.

2. The modular retractor of claim 1, wherein each primary blade of the plurality of primary blades is disposed around a circumference of the first annular retainer.

3. The modular retractor of claim 1, wherein each primary blade of the plurality of primary blades is configured to, selectively, pivotally couple to the adjacent primary blade of the plurality of primary blades by a ball and socket mechanism, the ball and socket mechanism being configured to facilitate the articulation.

4. The modular retractor of claim 3, wherein: each primary blade of the plurality of primary blades includes a corresponding primary blade retaining clip, each primary blade retaining clip being disposed at a top portion of each corresponding primary blade of the plurality of primary blades.

5. The modular retractor of claim 4, wherein:
each primary blade retaining clip comprises a first groove and a second groove, the first grooves of each primary blade retaining clip defining, together, a first pathway, the second grooves of each primary blade retaining clip defining, together, a second pathway,
the first annular retainer is operably coupled to each primary blade of the plurality of primary blades via the first pathway, and
the second annular retainer is operably coupled to each primary blade of the plurality of primary blades via the second pathway.

6. The modular retractor of claim 5, wherein:
the first annular retainer, in a first mode of operation, is configured to radially contract within the first passageway and towards the first center point such that each primary blade of the plurality of primary blades articulates away from the central axis due to an applied radial force, and
the first annular retainer, in a second mode of operation, is configured to release the applied radial force and return the primary blades to an initial position.

7. The modular retractor of claim 6, wherein the second annular retainer applies the biasing force to the plurality of primary blades via the second pathway such that when the first annular retainer, in the second mode of operation, releases the applied radial force the biasing force facilitates the return of the primary blades to the initial position.

8. The modular retractor of claim 1, wherein the contraction mechanism comprises: a sliding actuator, a turnbuckle, and/or a set screw and a sliding ring.

9. A modular retractor, comprising:
a first annular retainer and a second annular retainer, the first annular retainer defining a first center point and the second annular retainer defining a second center point;
a central axis projecting through the first center point and the second center point;
a plurality of primary blades, the plurality of primary blades being coupled to the first annular retainer, each primary blade of the plurality of primary blades being configured to, selectively, pivotally couple to an adjacent primary blade of the plurality of primary blades; and
at least one supplemental blade,
wherein the first annular retainer is configured to, selectively, radially contract towards the first center point such that each primary blade of the plurality of primary blades articulates with respect to the central axis,
wherein the second annular retainer circumscribes the outside of the plurality of primary blades and is configured to apply a biasing force against each primary blade of the plurality of primary blades towards the central axis,
wherein each supplemental blade of the at least one supplemental blade is configured to, selectively, pivotally couple to a pair of primary blades of the plurality of primary blades and the first annular retainer,
wherein the first annular retainer is further configured to, selectively, radially contract towards the first center point such that each primary blade of the plurality of primary blades and each supplemental blade of the at least one supplemental blade articulates with respect to the central axis, and
wherein the second annular retainer circumscribes the outside of the plurality of primary blades and each supplemental blade of the at least one supplemental blade, the second annular retainer being further configured to apply a biasing force against each primary blade of the plurality of primary blades and each supplemental blade of the at least one supplemental blade towards the central axis.

10. The modular retractor of claim 9, wherein:

each supplemental blade of the at least one supplemental blade comprises a corresponding supplemental blade retaining clip, each supplemental blade retaining clip being disposed at a top portion of each supplemental blade of the at least one supplemental blade, each supplemental blade retaining clip comprises a first groove and a second groove, each primary blade of the plurality of primary blades comprises a corresponding primary blade retaining clip, each primary blade retaining clip being disposed at a top portion of each primary blade of the plurality of primary blades, each primary blade retaining clip comprises a first groove and a second groove, the first grooves of each supplemental blade retaining clip and the first grooves of each primary blade retaining clip defining, together, a first pathway, and the second grooves of each primary blade retaining clip defining, together, a second pathway, the first annular retainer is operably coupled to each supplemental blade of the at least one supplemental blade and each primary blade of the plurality of primary blades via the first pathway, and the second annular retainer is operably coupled to each supplemental blade of the at least one supplemental blade and each primary blade of the plurality of primary blades via the second pathway.

11. The modular retractor of claim 10, wherein:

each supplemental blade of the at least one supplemental blade includes an outside surface, an inside surface opposite the outside surface, a first sidewall surface and a second sidewall surface opposite the first sidewall surface, the first sidewall surface and the second sidewall surface each extending between the outside surface and the inside surface, each first sidewall surface includes a first protrusion projecting away from the first sidewall surface, and each second sidewall surface includes a second protrusion projecting away from the second sidewall surface.

12. The modular retractor of claim 11, wherein:

each primary blade of the plurality of primary blades includes a first recess disposed on the corresponding first sidewall surface at an end portion of the corresponding first channel, and each primary blade of the plurality of primary blades includes a second recess disposed on the corresponding second sidewall surface at an end portion of the corresponding second channel.

13. The modular retractor of claim 12, wherein:

each first protrusion is configured to engage, selectively, with a corresponding first recess, and each second protrusion is configured to engage, selectively, with a corresponding second recess.

14. The modular retractor of claim 9, wherein:

each primary blade of the plurality of primary blades includes an outside surface, an inside surface opposite the outside surface, a first sidewall surface and a second sidewall surface opposite the first sidewall surface, the first sidewall surface and the second sidewall surface each extending between the outside surface and the inside surface, each first sidewall surface includes a first channel extending, at least partly, along the first sidewall surface, and each second sidewall surface includes a second channel extending, at least partly, along the second sidewall surface.

15. A modular retractor system, comprising:

a first annular retainer and a second annular retainer, the first annular retainer defining a first center point and the second annular retainer defining a second center point;

a central axis projecting through the first center point and the second center point;

a plurality of primary blades, the plurality of primary blades being coupled to the first annular retainer, each primary blade of the plurality of primary blades being configured to, selectively, pivotally couple to an adjacent primary blade of the plurality of primary blades; and a plurality of supplemental blades, each supplemental blade of the plurality of supplemental blades being configured to, selectively, in an installed position, pivotally couple to a pair of adjacent primary blades of the plurality of primary blades and the first annular retainer, wherein the first annular retainer is configured to, selectively, radially contract towards the first center point such that each primary blade of the plurality of primary blades articulates with respect to the central axis and each supplemental blade of the plurality of supplemental blades, in the installed position, articulates with respect to the central axis, and wherein the second annular retainer circumscribes the outside of the plurality of primary blades and the outside of each supplemental blade of the plurality of supplemental blades in the installed position, the second annular retainer being configured to apply a biasing force against each primary blade of the plurality of primary blades and each supplemental blade of the plurality of supplemental blades, in the installed position, towards the central axis.

16. The modular retractor system of claim 15, wherein:

each supplemental blade of the plurality of supplemental blades comprises a corresponding supplemental blade retaining clip, each supplemental blade retaining clip being disposed at a top portion of each supplemental blade of the plurality of supplemental blades, each supplemental blade retaining clip comprises a first groove and a second groove, each primary blade of the plurality of primary blades comprises a corresponding primary blade retaining clip, each primary blade retaining clip being disposed at a top portion of each primary blade of the plurality of primary blades, each primary blade retaining clip comprises a first groove and a second groove, the first grooves of each supplemental blade retaining clip and the first grooves of each primary blade retaining clip defining, together, a first pathway, and the second grooves of each primary blade retaining clip defining, together, a second pathway, the first annular retainer is operably coupled to each supplemental blade of the at least one supplemental blades and each primary blade of the plurality of primary blades via the first pathway, and the second annular retainer is operably coupled to each supplemental blade of the at least one supplemental blades and each primary blade of the plurality of primary blades via the second pathway.

17. The modular retractor system of claim 15, wherein:

each primary blade of the plurality of primary blades includes a first outside surface, a first inside surface opposite the first outside surface, a first sidewall surface and a second sidewall surface opposite the first sidewall surface, the first sidewall surface and the second sidewall surface each extending between the outside surface and the inside surface, each supplemental blade of the plurality of supplemental blades includes a second outside surface, and a second inside surface opposite the outside surface, a third sidewall surface and a fourth sidewall surface opposite the third sidewall surface, the third sidewall surface and the fourth sidewall surface each extending between the second outside surface and the second inside surface, each first sidewall surface of each primary blade includes a first channel extending, at least partly, along the first sidewall surface of the corresponding primary blade, each second sidewall surface of each primary blade includes a second channel extending, at least partly, along the second sidewall surface of the corresponding primary blade, each third sidewall surface of each supplemental blade includes a first protrusion projecting away from the third sidewall surface, and each fourth sidewall surface of each supplemental blade includes a second protrusion projecting away from the fourth sidewall surface.

18. The modular retractor system of claim 17, wherein:

each primary blade of the plurality of primary blades includes a first recess disposed on the corresponding first sidewall surface at an end portion of the corresponding first channel, and each primary blade of the plurality of primary blades includes a second recess disposed on the corresponding second sidewall surface at an end portion of the corresponding second channel.

19. The modular retractor system of claim 18, wherein:

each first protrusion is configured to engage, selectively, with a corresponding first recess, and each second protrusion is configured to engage, selectively, with a corresponding second recess.

\* \* \* \* \*